US012796895B2

(12) United States Patent
Ding et al.

(10) Patent No.: US 12,796,895 B2
(45) Date of Patent: Nov. 17, 2026

(54) CONNECTING DEVICES AND ENDOSCOPE CONNECTING SYSTEMS

(71) Applicant: JIANGSU VEDKANG MEDICAL SCIENCE AND TECHNOLOGY CO., LTD., Changzhou (CN)

(72) Inventors: Qiushi Ding, Changzhou (CN); Hualing Lu, Changzhou (CN)

(73) Assignee: JIANGSU VEDKANG MEDICAL SCIENCE AND TECHNOLOGY CO., LTD., Changzhou (CN)

( * ) Notice: Subject to any disclaimer, the term of this patent is extended or adjusted under 35 U.S.C. 154(b) by 58 days.

(21) Appl. No.: 19/071,745

(22) Filed: Mar. 5, 2025

(65) Prior Publication Data

US 2026/0090700 A1 Apr. 2, 2026

Related U.S. Application Data

(63) Continuation-in-part of application No. PCT/CN2024/122899, filed on Sep. 30, 2024.

(51) Int. Cl.

*A61B 1/00* (2006.01)
*A61B 1/012* (2006.01)

(52) U.S. Cl.

CPC ...... *A61B 1/00128* (2013.01); *A61B 1/00105* (2013.01); *A61B 1/0014* (2013.01); *A61B 1/0125* (2013.01)

(58) Field of Classification Search

CPC .............. A61B 1/00128; A61B 1/0014; A61B 1/00105; A61B 1/0125; A61B 1/00142; A61B 1/00135; A61B 1/00154

See application file for complete search history.

(56) References Cited

U.S. PATENT DOCUMENTS

| | | | | |
|---|---|---|---|---|
| 9,560,954 | B2 | 2/2017 | Jacobs et al. | |
| 2010/0178014 | A1* | 7/2010 | Iwamizu ............ | A61B 1/00165 385/89 |
| 2019/0380562 | A1* | 12/2019 | Deuel ................ | A61B 1/00066 |
| 2020/0245853 | A1 | 8/2020 | Wang et al. | |
| 2020/0288952 | A1* | 9/2020 | Jurevicius ............ | A61B 1/0055 |
| 2022/0354343 | A1 | 11/2022 | Brechbiel et al. | |
| 2024/0164633 | A1* | 5/2024 | Johnson ............. | A61B 1/00137 |
| 2025/0072726 | A1 | 3/2025 | Li et al. | |

FOREIGN PATENT DOCUMENTS

| | | | | |
|---|---|---|---|---|
| CN | 116350151 | A | * | 2/2023 |
| CN | 220556369 | U | | 3/2024 |
| CN | 221712237 | U | | 9/2024 |

* cited by examiner

*Primary Examiner* — Michael J Carey
*Assistant Examiner* — Dayton Hyun Jin Barker
(74) *Attorney, Agent, or Firm* — PORUS IP LLC

(57) ABSTRACT

A connecting device and an endoscopic connecting system are provided. The connecting device includes a first connecting portion and a second connecting portion. The first connecting portion is configured to connect a baby endoscope. The second connecting portion is connected to the first connecting portion. The second connecting portion encloses to form a socket cavity and is connected to a first opening and a second opening of the socket cavity. An area of a cross-section of the second connecting portion progressively increases in a direction from the first opening to the second opening. The second combination part is configured to be socketed to a mother endoscope through the socket cavity and is connected with the mother endoscope.

14 Claims, 8 Drawing Sheets

CONNECTING DEVICES AND ENDOSCOPE CONNECTING SYSTEMS

CROSS-REFERENCE TO RELATED APPLICATIONS

This application is a Continuation-in-part of International Application No. PCT/CN2024/122899, filed on Sep. 30, 2024, the entire contents of which are hereby incorporated by reference.

TECHNICAL FIELD

The present disclosure relates to the technical field of medical devices, and in particular, to connecting devices and endoscope connecting systems.

BACKGROUND

Endoscopes are differentiated according to the scene of use, which may include bronchoscopes, enteroscopes, gastroscopes, etc. Endoscopes are simply examination instruments, and usually consist of two parts of structures, i.e., a handle and an imaging catheter that is connected to the handle. The imaging catheter is provided with a camera at the front end, and the imaging catheter is photographed or videotaped after it enters the natural lumen of the human body. The images captured by the camera are transmitted optically to a host monitor connected to the endoscope handle, which facilitates the doctor to observe the presence of diseased tissue (e.g., polyps, early cancers, etc.) in the natural lumen of the human body. The endoscope does not have a surgical function. If the doctor discovers diseased tissue with the help of the camera of the imaging catheter, the imaging catheter is usually set up with a lumen of the instrument, and there is a pincer hole set up on the handle, which is connected to the lumen of the instrument. When encountering diseased tissue that needs to be handled, such as a polyp, and the polyp needs to be removed, it is necessary to insert an endoscopic minimally invasive surgical consumable device such as a snare from the pincer hole through the imaging catheter to reach the target diseased tissue and then perform a polyp removal procedure. After removing the polyp, the snare is withdrawn from the endoscope handle, and if bleeding is found in the imaging catheter lens, a hemostatic clip needs to be inserted from the pincer hole, and the hemostatic clip is released to complete the tissue clamping to stop the bleeding by compression.

Choledochoscope, an examination instrument for the diagnosis and treatment of diseases occurring in the biliary tract (e.g. gallstones). The biliary tract is elongated and narrow, and common endoscopes, such as duodenoscopes, with imaging catheters approaching 2 cm in diameter, are clearly unsuitable for direct management of diseased biliary tract tissue. The choledochoscope (which also includes a handle and an imaging catheter, with the handle also provided with a pincer hole and the imaging catheter also provided with an instrument lumen) is used as a minimally invasive surgical consumable type of instrument just like the aforementioned snare and the hemostatic clip, where the imaging catheter of the choledochoscope is inserted into the pincer hole of the endoscope (usually duodenoscopy), and then further accessed to the biliary tract through the imaging catheter of the duodenoscopy (diameter of the imaging catheter of the choledochoscope generally within 3 millimeters) for stone removal or biopsy operations.

It is clear from the above that the choledochoscope, as a baby endoscope of the duodenoscope (also known as the mother endoscope), is used in conjunction with the duodenoscope and not independently. During procedure, the surgeon needs to hold both the duodenoscope and the choledochoscope at the same time. Once the mother endoscope (duodenoscope) reaches the vicinity of the biliary tract, it cannot be moved at will. Thus, it is necessary to maintain relative fixation between the baby endoscope (choledochoscope) and the mother endoscope (duodenoscope) while performing the procedure.

Therefore, a connecting device is provided that is capable of maintaining relative fixation between a baby endoscope and a mother endoscope.

SUMMARY

One or more embodiments of the present disclosure provide a connecting device. The connecting device may include a first connecting portion configured to connect a baby endoscope and a second connecting portion connected to the first connecting portion. The second connecting portion may enclose to form a socket cavity. The second connecting portion may be connected to a first opening and a second opening of the socket cavity. An area of a cross-section of the socket cavity may increase in a direction from the first opening to the second opening. The second connecting portion may be configured to be socketed to a mother endoscope through the socket cavity. The second connecting portion may be connected with the mother endoscope.

In some embodiments, the second connecting portion may be provided in any one of the following ways: the second connecting portion may be a closed ring, and an outer wall of the second connecting portion may be connected to the first connecting portion; the second connecting portion may be provided with a first notch, the first notch may be connected to the socket cavity, the first notch may extend from the first opening to the second opening, and a side of the second connecting portion opposite the first notch may be connected to the first connecting portion.

In some embodiments, the first connecting portion may include a main housing and a plurality of tabs. The second connecting portion may be connected to the main housing. Each of the plurality of tabs may be connected to the main housing, and each of the plurality of tabs may be spaced in turn along a circumference of an edge of the main housing. In a state in which the first connecting portion is connected with the baby endoscope, the main housing may be affixed to the baby endoscope, and each of the plurality of tabs may be snap-fit to an outer wall surface of a medical device.

In some embodiments, two sides of the first connecting portion may be provided with a first side edge and a second side edge along a width direction. A distance between the second connecting portion and the first side may be less than a distance between the second connecting portion and the second side edge.

One of the embodiments of the present disclosure provides an endoscope connecting system. The endoscope connecting system may include the connecting device and the baby endoscope detachably connected with the first connecting portion of the connecting device.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures, and wherein.

Figure 1:
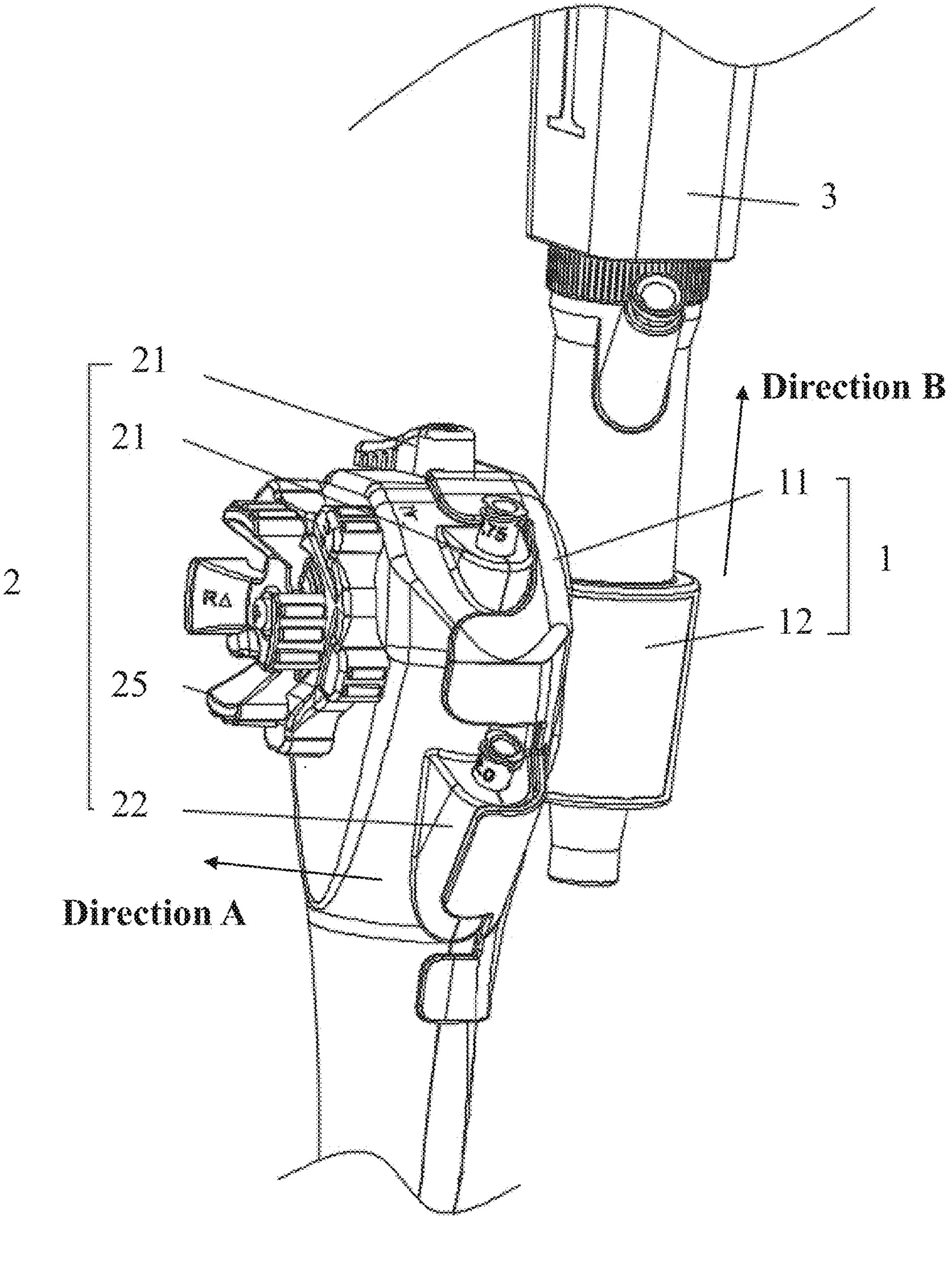
FIG. 1 is a schematic diagram illustrating a connecting device, a baby endoscope, and a mother endoscope according to some embodiments of the present disclosure.

Figures: 1, connecting device; 11, first connecting portion; 111, main housing; 1111, reinforcing rib; 1112, reinforcing back plate; 112, tab; 113, first side edge; 114, second side edge; 12, second connecting portion; 121, first opening; 122, second opening; 123, first notch; 124, first sub connecting portion; 125, second sub connecting portion; 1241, first end; 1242, second end; 1251, third end; 1252, fourth end; 126, locking structure; 13, sheath; 131, sheath body; 132, port wrapping rib; 133, second notch; 134, notch wrapping rib; 2, baby endoscope; 21, functional portion; 22, pincer channel nozzle; 25, rotating wheel; 3, mother endoscope; 4, processor; 51, first pressure sensor; 52, second pressure sensor; 53, displacement sensor.

DETAILED DESCRIPTION

To more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that “system”, “device”, “unit” and/or “module” as used herein is a manner used to distinguish different components, elements, parts, sections, or assemblies at different levels. However, if other words serve the same purpose, the words may be replaced by other expressions.

As shown in the present disclosure and claims, the words “one”, “a”, “a kind” and/or “the” are not especially singular but may include the plural unless the context expressly suggests otherwise. In general, the terms “comprise”, “comprises”, “comprising”, “include”, “includes”, and/or “including”, merely prompt to include operations and elements that have been clearly identified, and these operations and elements do not constitute an exclusive listing. The methods or devices may also include other operations or elements.

FIG. 1 is a schematic diagram illustrating a connecting device, a baby endoscope, and a mother endoscope according to some embodiments of the present disclosure.

In some embodiments, as shown in FIG. 1, the connecting device 1 refers to a device for connecting a baby endoscope 2 to a mother endoscope 3, such that the two are fixed in a relative position. The doctor only needs to hold one of the baby endoscope 2 or the mother endoscope 3, which reduces the difficulty of surgical operation.

The mother endoscope 3 refers to an instrument having an imaging catheter with a larger diameter. The baby endoscope 2 refers to an instrument having an imaging catheter with a smaller diameter, which is used in conjunction with the mother endoscope 3. For example, a choledochoscope, as a sub scope of a duodenoscope (also known as main scope), may be used in conjunction with the duodenoscope. During the operation, the doctor holds the duodenoscope and choledochoscope at the same time, and after the main scope (duodenoscope) reaches the vicinity of the biliary tract, it cannot be moved arbitrarily, and the relative position between the sub scope (choledochoscope) and the main scope (duodenoscope) is kept fixed, which reduces the difficulty of the surgical operation.

Figure 2:
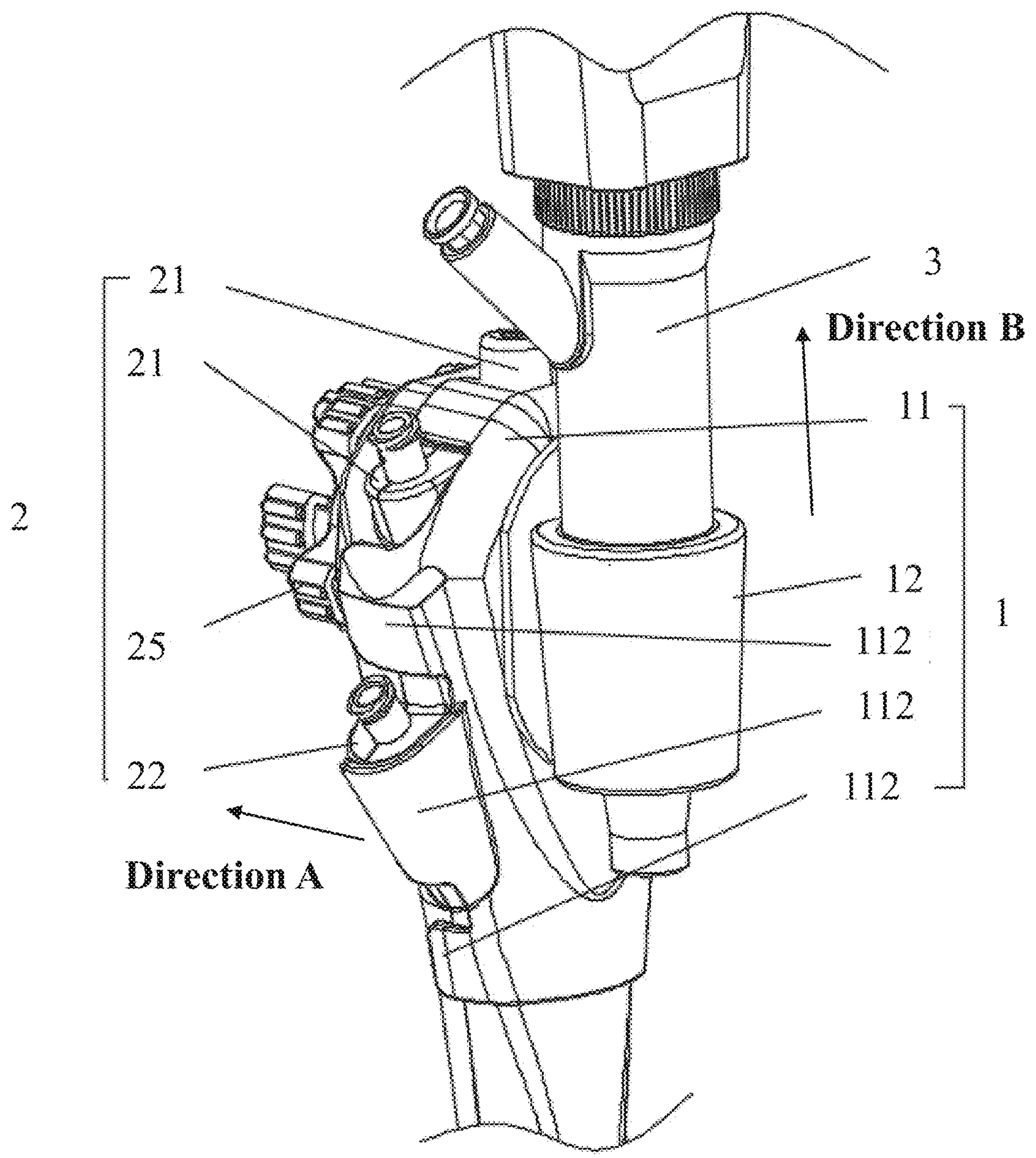
FIG. 2 is a schematic diagram illustrating another connecting device, another baby endoscope, and another mother endoscope according to some embodiments of the present disclosure.

FIG. 2 is a schematic diagram illustrating another connecting device, another baby endoscope, and another mother endoscope according to some embodiments of the present disclosure.

Figure 3:
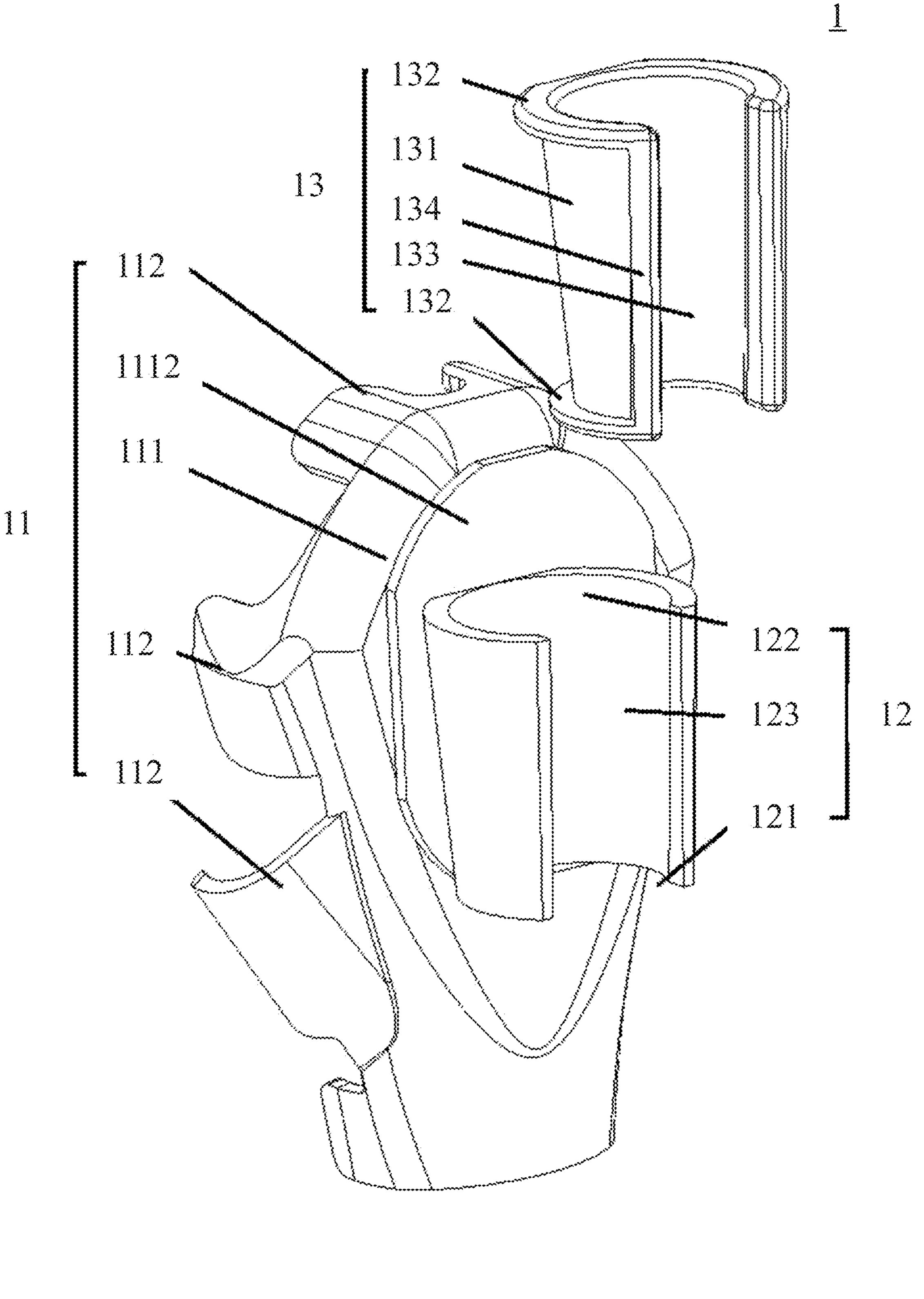
FIG. 3 is a schematic diagram illustrating an exemplary connecting device according to some embodiments of the present disclosure.

In some embodiments, as shown in FIG. 1 to FIG. 3, the connecting device 1 may include a first connecting portion 11 and a second connecting device 12. The first connecting portion 11 is configured to connect the baby endoscope 2. The second connecting portion 12 is connected to the first connecting portion 11. One side of the second connecting portion 12 is connected to the first connecting portion 11, and the other side of the second connecting portion 12 is connected to the mother endoscope 3. The second connecting portion 12 is detachably connected with the mother endoscope 3.

In some embodiments, the first connecting portion 11 may be detachably connected with the baby endoscope 2, and the second connecting portion 12 may also be detachably connected with the mother endoscope 3. Merely by way of example, at the end of a procedure, an operator may detach the first connecting portion 11 from the baby endoscope 2 and detach the second connecting portion 12 from the mother endoscope 3, thereby facilitating the cleaning and storing of the baby endoscope 2 and the mother endoscope 3, respectively.

In some embodiments, the mother endoscope 3 may be a colonoscope or a gastroscope. In the example where the mother endoscope 3 is a duodenoscope, the baby endoscope 2 may be a choledochoscope used in conjunction with the duodenoscope. During the procedure, the doctor inserts the imaging catheter of the duodenoscope into the natural lumen of the human body and then takes a picture or video, so that the doctor may easily observe the presence of diseased tissue (e.g., polyps, early cancers, etc.) in the natural lumen of the human body. If the doctor finds diseased tissue, the imaging catheter of the choledochoscope needs to be inserted into a pincer channel nozzle of the duodenoscope, and through the imaging catheter of the duodenoscope, the imaging catheter of the choledochoscope is further accessed into the biliary tract to perform a stone removal or biopsy operation. During the procedure, in order to reduce the difficulty of the operation, the operator may pre-connect the connecting device 1 to the choledochoscope through the first connecting portion 11, and when the choledochoscope is used later, the connecting device 1 may be connected to the duodenoscope through the second connecting portion 12 quickly and efficiently in conjunction with the duodenoscope. Therefore, the doctor may hold the duodenoscope and the choledochoscope in one hand, which facilitates the doctor's operation of the choledochoscope for procedure.

In some embodiments, as shown in FIGS. 1-3, the second connecting portion 12 encloses to form a socket cavity, the second connecting portion 12 is connected to a first opening 121 and a second opening 122 of the socket cavity, and an area of a cross-section of the socket cavity progressively increases in a direction from the first opening to the second opening. The second connecting portion 12 is configured to be socketed to the mother endoscope 3 through the socket cavity, and the second connecting portion 12 is connected with the mother endoscope 3. The socket cavity refers to a cavity space for snapping the mother endoscope 3. The first opening 121 and the second opening 122 are disposed at two ends of the second connecting portion 12.

In some embodiments, the second connecting portion 12 may be of a tapered barrel structure. When the mother endoscope 3 is a gastroscope or a colonoscope, a tapered transition segment is provided between the handle and the imaging catheter. The tapered transition segment has a large head end near the handle. In some embodiments, the socket cavity of the second connecting portion 12 is a tapered cavity. After the second connecting portion 12 is socketed to the imaging catheter of the mother endoscope 3, the second connecting portion continues to move toward the handle of the second connecting portion 12. Therefore, the second connecting portion 12 and the tapered transition segment of the mother endoscope 3 may be in close contact, thereby realizing a connection fit between the second connecting portion 12 and the mother endoscope 3, and the extrusion fit between the second connecting portion 12 and the tapered transition segment, which has a large frictional resistance and gripping force, and the connecting device 1 may not be easily detached from the tapered transition segment of the mother endoscope 3. In some embodiments, the second connecting portion 12 may be in other shapes that match the mother endoscope 3. For example, when the mother endoscope 3 is provided with a plurality of tapered transition segments, the second connecting portion 12 may be a plurality of tapered cylinders with different diameter transitions.

Figure 4:
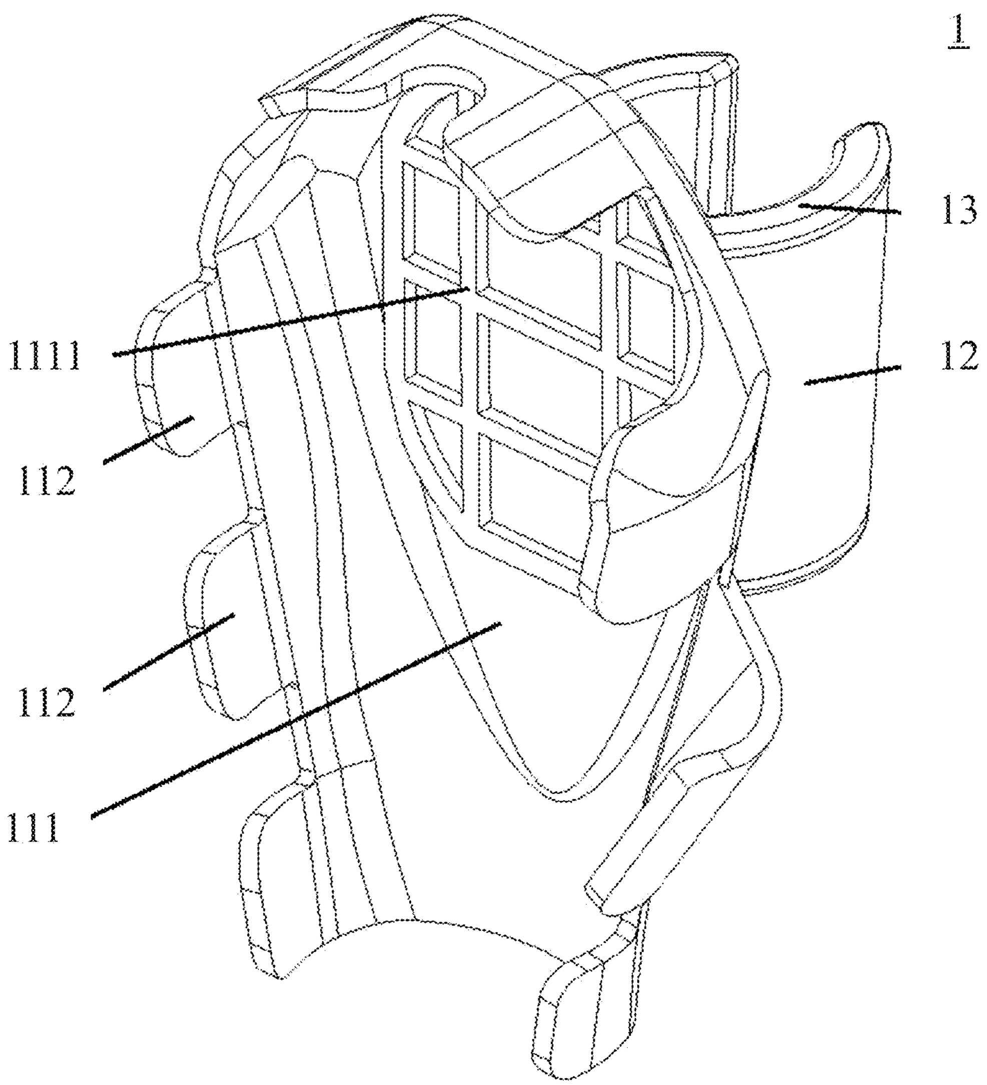
FIG. 4 is a schematic diagram illustrating another exemplary connecting device according to some embodiments of the present disclosure.
Figure 5:
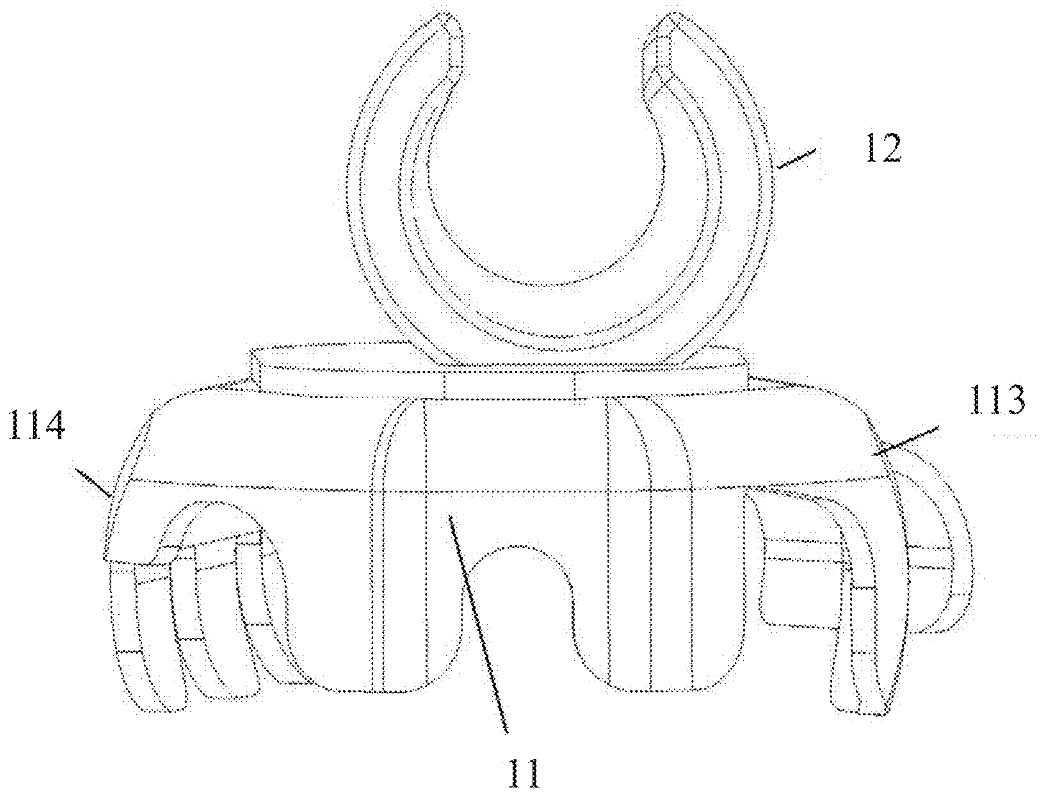
FIG. 5 is a schematic diagram illustrating yet another exemplary connecting device according to some embodiments of the present disclosure.
Figure 6:
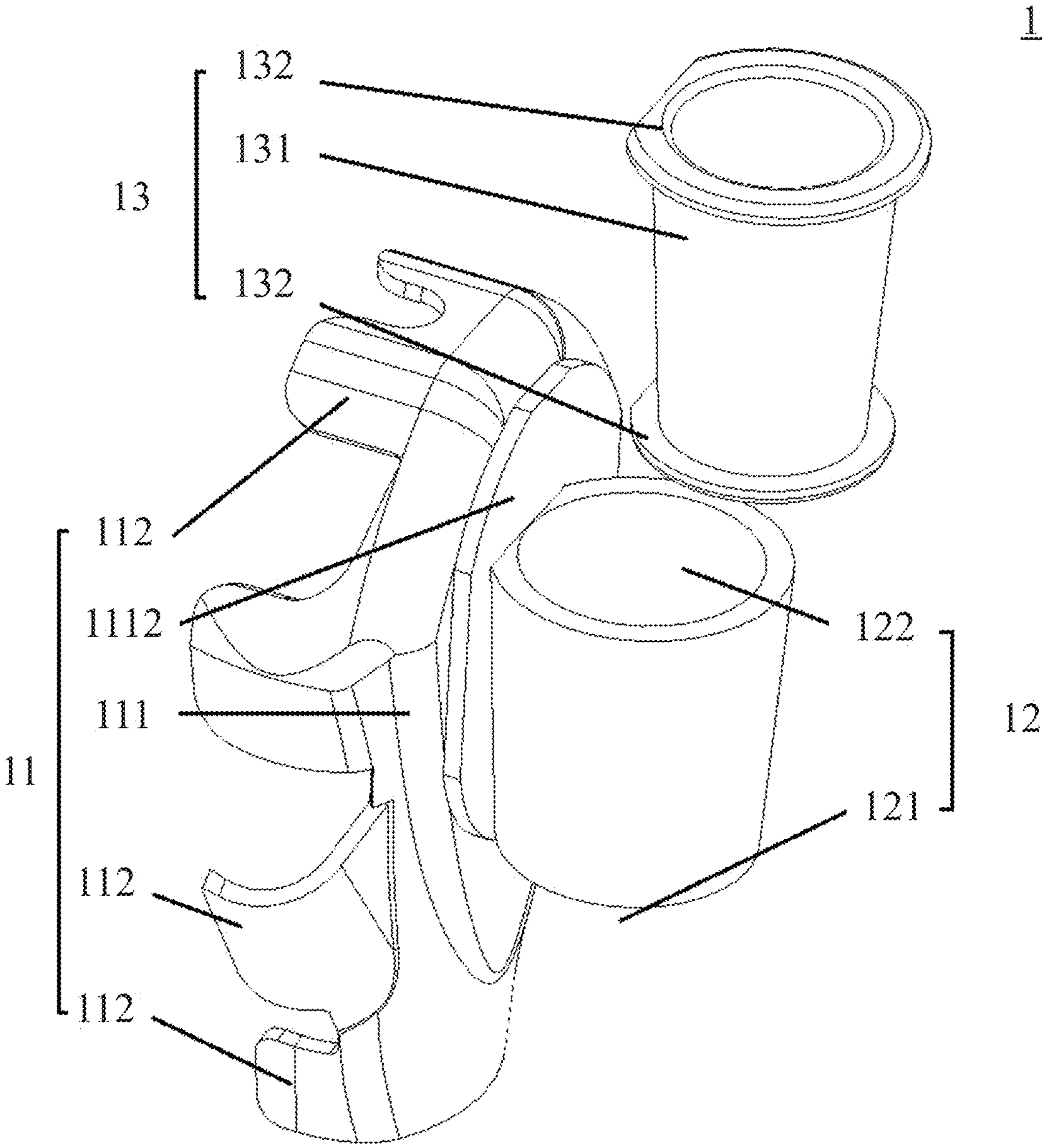
FIG. 6 is an exploded view illustrating an exemplary connecting device according to some embodiments of the present disclosure.

FIG. 4 is a schematic diagram illustrating another exemplary connecting device according to some embodiments of the present disclosure. FIG. 5 is a schematic diagram illustrating yet another exemplary connecting device according to some embodiments of the present disclosure. FIG. 6 is an exploded view illustrating an exemplary connecting device according to some embodiments of the present disclosure In some embodiments, the second connecting portion 12 may be set up in either of the following two ways. In the first setup, referring to FIG. 6, the second connecting portion 12 is in the shape of a closed ring, and the outer wall of the second connecting portion 12 is connected to the first connecting portion 11. The second connecting portion 12 may be a conical cylinder, and the second connecting portion 12 needs to be pre-socketed and fixed to a conical transition segment of the mother endoscope 3 before the procedure, and when the baby endoscope 2 needs to be used, the doctor then assembles the baby endoscope 2 to the first connecting portion 11. In some embodiments, the outer wall of the second connecting portion 12 may be connected to the first connecting portion 11 in a variety of ways. For example, the outer wall of the second connecting portion 12 is integrally molded to the first connecting portion 11. As another example, the outer wall of the second connecting portion 12 is connected to the first connecting portion 11 by welding, screwing, gluing, or the like.

In the second setup, as shown in FIG. 3 and FIG. 4, the second connecting portion 12 is provided with a first notch 123, the first notch 123 is connected to the socket cavity, and the first notch 123 extends from the first opening 121 to the second opening 122. The side of the second connecting portion 12 opposite the first notch 123 is connected to the first connecting portion 11. That is, the side of the second connecting portion 12 that is away from the first notch 123 is connected to the first connecting portion 11.

In the second setup, the second connecting portion 12 is not a closed cylinder, but a conical cylinder having an elongated first notch 123. In some embodiments, the first notch 123 may be an elongate opening, and the width of the first notch 123 is not less than an outer diameter of a localized structure (the imaging catheter) of the mother endoscope 3, allowing the mother endoscope 3 to extend into the socket cavity through the elongate opening. In the second setup, instead of assembling the connecting device 1 to the mother endoscope 3 in advance, the connecting device 1 may be first assembled and connected to the baby endoscope 2 through the first connecting portion 11. During the procedure, when the baby endoscope 2 is needed, the second connecting portion 12 is then assembled and connected to the mother endoscope 3. In a specific operation process, an operator (e.g., a doctor) may move the connecting device 1 so that the imaging catheter of the mother endoscope 3 passes through the first notch 123 into the socket cavity of the second connecting portion 12, and then move the connecting device 1 upwardly, so that the second connecting portion 12 may be tightly snapped onto the tapered transition segment of the mother endoscope 3. When it is necessary to disengage the paired state of use, the mother endoscope 3 may be moved upwardly with respect to the connecting device 1, and the mother endoscope 3 may be quickly detached from the connecting device 1. In some embodiments, when the second connecting portion 12 has a certain elasticity, the width of the first notch 123 may refer to the width when the first notch 123 is stretched open. A width direction of the first notch 123 is perpendicular to a direction of a line connecting the first opening 121 and the second opening 122.

In some embodiments, referring to FIG. 3, the connecting device 1 may include a sheath 13, and the sheath 13 is a flexible body. The sheath 13 is at least partially disposed within the socket cavity, and, in a state in which the second connecting portion 12 is connected with the mother endoscope 3, the sheath 13 is compressed between the mother endoscope 3 and an inner wall of the socket cavity.

The sheath 13 may be made of an elastic material (e.g., silicone, rubber material). In a state in which the tapered transition segment of the mother endoscope 3 penetrates the second connecting portion 12, one side of the sheath 13 along the thickness direction is adhered to the surface of the tapered transition segment, and the other side of the sheath 13 along the thickness direction is adhered to the inner wall of the socket cavity. The sheath 13 serves as a cushioning and protective function. For example, the inner wall of the sheath 13 is adhered to the inner wall of the socket cavity, and the inner wall is adhered to the tapered transition segment of the mother endoscope 3. The inner wall of the sheath 13 is squeezed by the mother endoscope 3, and the outer surface of the sheath 13 is squeezed by the inner wall of the socket cavity, thereby providing cushioning protection.

In some embodiments, referring to FIG. 3, the sheath 13 has a sheath body 131 and port wrapping ribs 132. The sheath body 131 includes two ports, and the two ports are each provided with the port wrapping ribs 132. In the state in which the sheath 13 is connected to the second connecting portion 12, the sheath body 131 is affixed to the inner wall of the socket cavity, and the two port wrapping ribs 132 are provided over an end face of an edge of the first opening 121 of the second connecting portion 12 and an end face of an edge of the second opening 122 of the second connecting portion part 12, respectively.

In some embodiments, the port wrapping ribs 132 protrude from the outer surface of the sheath body 131. In the state in which the sheath 13 is connected with the second connecting portion 12, the sheath body 131 is located on an inner side of the socket cavity, and the ports at two ends of the sheath body 131 are directly covered on the end faces of the ports of the second connecting portion 12. Thus, direct contact of sharp prongs on the end faces and the mother endoscope 3 is avoided, which may cut or damage the mother endoscope 3.

It should be noted that, as shown in FIG. 6, when the second connecting portion 12 is a closed cylinder structure, the sheath 13 may be correspondingly set to a closed annular cylinder structure. Referring to FIG. 3, when the second connecting portion 12 is a barrel structure having an opening, the sheath 13 may be correspondingly provided as a barrel structure having an opening.

In some embodiments, as shown in FIG. 3, a second notch 133 is provided on the sheath body 131, and the second notch 133 is connected to each of the two ports. The sheath 13 has notch wrapping ribs 134 disposed on the sheath body 131, and the notch wrapping ribs 134 are disposed at the edge of the second notch 133. In the state in which the sheath 13 is connected with the second connecting portion 12, the notch wrapping ribs 134 cover an end face in the thickness direction of the first notch 123 of the second connecting portion 12. The end face in the thickness direction of the first notch 123 refers to a surface of a thickness direction formed between an inner wall and an outer wall of the second connecting portion 12. That is, the edge in the thickness direction of the first notch 123 of the second connecting portion 12 is covered by the notch wrapping ribs 134.

In some embodiments, the sheath 13 is not a closed barrel structure. In the state in which the sheath 13 is connected to the second connecting portion 12, the second notch 133 and the first notch 123 are positioned opposite each other, and the second notch 133 and the first notch 123 are connected. In other words, the second notch 133 and the first notch 123 are disposed at the same position. The second notch 133 and the first notch 123 form a notch for the second connecting portion 12 to be assembled and connected to the mother endoscope 3. The notch wrapping ribs 134 on the two edges of the second notch 133 protrude out of the outer surface of the sheath body 131, which may smoothly cover the end face in the thickness direction of the first notch 123 of the sheath body 131.

In some embodiments, as shown in FIGS. 2-6, the first connecting portion 11 includes a main housing 111 and a plurality of tabs 112, the second connecting portion 12 is connected to the main housing 111, each of the plurality of tabs 112 is connected to the main housing 111, and each of the plurality of tabs 112 is spaced in turn along a circumference of the edge of the main housing 111. In a state in which the first connecting portion 11 is connected with the baby endoscope 2, the main housing 111 is affixed to the baby endoscope 2, and each of the plurality of tabs 112 is snap-fit to an outer wall surface of a medical device. The spacing of the setting of the plurality of tabs 112 may be the same or different. The shapes of the plurality of tabs 112 may be different. For example, the shape of the tabs 112 set at the corners of the main housing 111 may be L-shaped bends. As another example, the shape of the tabs 112 may be rectangles with chamfered edges.

In some embodiments, a clamping space is formed by enclosing between each of the plurality of tabs 112 of the first connecting portion 11. The baby endoscope 2 typically includes a handle, the shape of the handle matches the clamping space, and the handle has an outer contour that is slightly larger than the clamping space. In the process of loading the handle of the baby endoscope 2 into the clamping space, the handle of the baby endoscope 2 may hold up the plurality of tabs 112, and each of the plurality of tabs 112 deform. When the handle is completely inside the clamping space, each of the plurality of tabs 112 resumes deformation and clamps onto the handle, thereby connecting and fixing the handle and the first connecting portion 11. Each of the plurality of tabs 112 is elastically affixed to different positions of the handle, thereby firmly snap-fitting the connecting device 1 to the endoscopic sub scope 2.

In some embodiments, a rough friction layer is provided on the inner wall of each of the plurality of tabs 112, a rough friction layer is provided on the baby endoscope 2 at a position corresponding to each of the plurality of tabs 112, or rough friction layers are provided on both the inner wall of each of the plurality of tabs 112 and the position corresponding to each of the plurality of tabs 112 of the baby endoscope 2. The rough friction layer may include a rough surface, a velvet surface, a rough rubber surface, or the like. The rough surface may be obtained by roughening the surface of the original baby endoscope 2 or the inner wall of the card 112. In some embodiments, the tabs 112 of the baby endoscope 2 is provided with matching bumps or grooves at corresponding positions to be fixed with the tabs 112. The matching bumps or grooves refer to bumps or grooves that match the rough friction layer.

In some embodiments of the present disclosure, a rough friction layer is provided on an inner wall of each tab or a position of the baby endoscope corresponding to the tab, or matching bumps or grooves are provided on an inner wall of each tab or a position of the baby endoscope corresponding to the tab, which is conducive to further improving friction, and preventing accidental dislodgement or sliding during operation.

In some embodiments, referring to FIG. 4, the main housing 111 is provided with a reinforcing rib 1111 on a side of the main housing 111 back away from the second connecting portion 12. The reinforcing rib 1111 may include a plurality of interlocking ribs to form a grid-like reinforcing rib 1111, thereby strengthening the structural strength of the connection between the second connecting portion and each tab 112 and improving the overall stiffness of the connecting device 1 when in use.

In some embodiments, referring to FIG. 3, a reinforcing back plate 1112 is provided on a side of the main housing 111 back from each tab 112 (i.e., on a side of the main housing 111 near the second connecting portion 12), and the second connecting portion 12 is connected to the reinforcing back plate 1112. The setting of the reinforcing back plate 1112 increases the structural strength and stiffness of the main housing 111, improves the overall stiffness of the connecting device 1 when in use, minimizes the relative motion of the baby endoscope 2 and the mother endoscope 3, and makes the two form a one-piece structure when mated by the connecting device 1.

In some embodiments, the baby endoscope 2 has a plurality of functional portions 21, at least a portion of which is disposed on an opening formed between adjacent tabs 112 in the state in which the first connecting portion 11 is connected with the baby endoscope 2.

In some embodiments, when the baby endoscope 2 is a choledochoscope, the functional portions 21 may include a photo button, a locking control button, a fluid injection port, or the like. The position of each tab 112 may be set up to avoid the functional portions 21 without affecting the normal use of the baby endoscope 2.

In some embodiments, the baby endoscope 2 is provided with an outwardly protruding pincer channel nozzle 22, the pincer channel nozzle 22 having a pincer channel opening. In the state in which the first connecting portion 11 is connected with the baby endoscope 2, one of the plurality of tabs 112 is snapped to an outer wall surface of the pincer channel nozzle 22. The handle of the baby endoscope 2 is provided with a photo button, a locking control button, and a fluid injection port. The handle is also provided with the pincer channel opening, and the pincer channel opening is connected to a pincer channel of the baby endoscope 2, and the pincer channel opening 22 protrudes out of the handle and extends for a long distance along the smooth circumferential side of the handle. If the tab 112 is misaligned with the pincer channel opening 22, the connection between the first connecting portion 11 and the baby endoscope 2 is prone to be unstable, and it is easy to disengage the tab. In some embodiments, the dimension of the inner wall of one tab of the plurality of tabs 112 is the same as or smaller than the dimension of the outer wall of the pincer channel opening 22, such that the tab 112 may closely fit on the outer wall surface of the pincer channel opening 22 and does not block the pincer channel opening of the pincer channel nozzle 22. Therefore, each tab 112 on the first connecting portion 11 is evenly snapped to the handle of the baby endoscope 2, improving the stability of the assembly structure.

In some embodiments, referring to FIG. 5, two sides of the first connecting portion 11 are provided with a first side edge 113 and a second side edge 114 along a width direction. A distance between the second connecting portion 12 and the first side edge 113 is smaller than a distance between the second connecting portion 12 and the second side edge 114. That is, the second connecting portion 12 is closer to the first side edge 113 in the width direction of the first connecting portion 11. The width direction of the first connecting portion 11 refers to a direction perpendicular to an extension direction of the imaging catheter of the baby endoscope 2.

In some embodiments, when the baby endoscope 2 is a choledochoscope, the handle thereof is provided with a rotating wheel 25, the rotating wheel 25 being disposed at a side of the handle back away from the first connecting portion 11. By rotating the rotating wheel 25, a bending angle and a bending direction of an end of the imaging catheter of the baby endoscope 2 may be adjusted. In some embodiments, the second connecting portion 12 is not provided at a central position along the width direction of the first connecting portion 11 but is close to one of the two sides of the first connecting portion 11 (e.g., close to the first side edge 113), and the second connecting portion 12 is biased out of the central position to form a leverage structure. There is a certain distance between the second connecting portion 12 and a rotational axis of the rotating wheel 25, which increases the torque and is able to easily offset the torque of the rotating wheel 25 of the medical device during rotation. Thus, the baby endoscope 2 may not be subjected to excessive force when the rotating wheel 25 is rotated, and there may not be a large offset between the handle of the baby endoscope 2 and the mother endoscope 3, which improves the precision of operation of the procedure.

Some embodiments of the present disclosure further provide an endoscopic connecting system including the connecting device 1 and the baby endoscope 2 as described above, and the baby endoscope 2 is detachably connected with the first connecting portion 11 of the connecting device 1.

In some embodiments, the endoscopic connecting system further includes the mother endoscope 3, the mother endoscope 3 being detachably connected with the second connecting portion 12 of the connecting device 1.

In some embodiments, the first connecting portion 11 of the connecting device 1 of the endoscopic connecting system may be removably connected with the baby endoscope 2, and the second connecting portion 12 may also be connected with the mother endoscope 3. At the end of the procedure, the first connecting portion 11 may be detached from the baby endoscope 2, and the second connecting portion 12 may be detached from the mother endoscope 3, thereby facilitating the cleaning and storing of the baby endoscope 2 and the mother endoscope 3, respectively.

In some embodiments, the second connecting portion 12 of the connecting device 1 may be socketed to the mother endoscope 3 to realize the quick cooperation of the connecting device 1 and the mother endoscope 3. When it is necessary to dismantle the mother endoscope 3, it is necessary to only make the mother endoscope 3 move upward relative to the connecting device 1, so that the mother endoscope 3 and the connecting device 1 may be fixed relatively in a radial direction along the imaging catheter. The structure of the connecting device 1 is simple, and it is easy to cooperate and incoordinate the baby endoscope and the mother endoscope. The first connecting portion 11 of the connecting device 1 is snap-fitted to the baby endoscope 2 by the plurality of tabs 112.

In some embodiments, a disassembling direction of the baby endoscope 2 from the first connecting portion 11 is different from a disassembling direction of the mother endoscope 3 from the second connecting portion 12. When an external force is applied to the mother endoscope 3 to dismantle the connecting relationship between the mother endoscope 3 and the connecting device 1, the bonding relationship between the connecting device 1 and the baby endoscope 2 is not affected, and the connecting device 1 and the baby endoscope 2 may maintain the connection bonding state without being affected.

In some embodiments, the operator may dismantle the baby endoscope 2 from the first connecting portion 11 by applying a force along a horizontal direction (as in the direction A in FIGS. 1 and 2) of the operating handle of the baby endoscope 2. The term "along a horizontal direction of the operating handle of the baby endoscope 2" may be understood to be in a direction generally along the thickness direction of the operating handle, or in a direction in which the first connecting portion 11 and the second connecting portion 12 of the connecting device 1 are arranged.

An operator may dismantle the mother endoscope 3 from the second connecting portion 12 by applying a force along a vertical direction (as in the direction B of FIGS. 1 and 2) of the imaging catheter of the mother endoscope 3.

As can be seen, the dismantling direction the baby endoscope 2 from the first connecting portion 11 and the dismantling direction of the mother endoscope 3 from the second connecting portion 12 may be approximately perpendicular. Therefore, when one of the mother endoscope 3 and the baby endoscope 2 is dismantled by the external force, the combined connection state of the other and the connecting device 1 is not affected.

Figure 7:
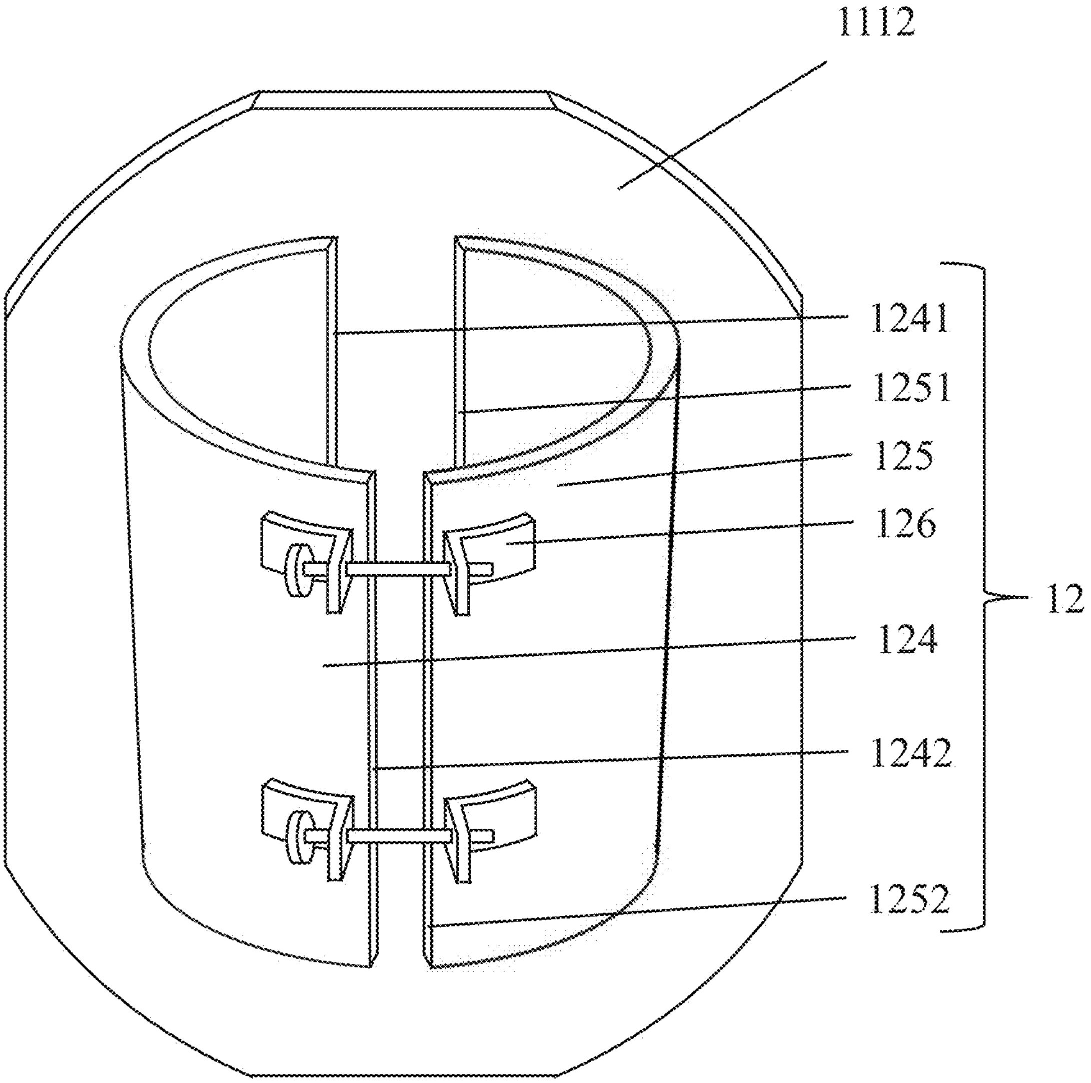
FIG. 7 is a schematic diagram illustrating a second connecting portion according to some embodiment of the present disclosure.

FIG. 7 is a schematic diagram illustrating a second connecting portion according to some embodiment of the present disclosure.

In some embodiments, as shown in FIG. 7, the second connecting portion 12 includes a first sub connecting portion 124 and a second sub connecting portion 125. Merely by way of example, the first sub connecting portion 124 and the second sub connecting portion 125 are semi-annular.

In some embodiments, the first sub connecting portion 124 includes a first end 1241 and a second end 1242, and the second sub connecting portion 125 may include a third end 1251 and a fourth end 1252.

The first end 1241 and the third end 1251 are portions of the first sub connecting portion 124 that remain in connection with the second sub connecting portion 125. In some embodiments, the first end 1241 of the first sub connecting portion 124 is in rotatable connection with the third end 1251 of the second sub connecting portion 125. The rotatable connection may be in a variety of ways. For example, the first end 1241 may be rotatably connected with the third end 1251 based on an axis of rotation. As another example, the first end 1241 is hinged with the third end 1251.

In some embodiments, the first end 1241 is not directly connected with the third end 1251, and both are rotatably connected with the reinforcing back plate 1112. For example, a rotational axis is provided on the reinforcing back plate 1112, and the first end 1241 and the third end 1251 are rotationally connected to the reinforcing back plate 1112 via the rotational axis.

The second end 1242 and the fourth end 1252 refer to portions of the first sub connecting portion 124 and the second sub connecting portion 125 that may be opened or closed. In some embodiments, the second end 1242 of the first sub connecting portion 124 and the fourth end 1252 of the second sub connecting portion 125 are held in place by a locking structure 126 when closed.

The locking structure 126 refers to a component for connecting and fixing the open and closed portions of the first sub connecting portion 124 and the second sub connecting portion 125. The locking structure 126 may include bolts, snaps, or the like. For example, the first sub connecting portion 124 and the second sub connecting portion 125 rotate at a certain angle through the rotational axis to form a circular tube-shaped cavity or a circular tube-shaped cavity with an opening, and the locking structure 126 locks the first sub connecting portion 124 and the second sub connecting portion 125 in a fixed position. Merely by way of example, as shown in FIG. 7, the locking structure 126 is a bolt, and the operator adjusts the bolt to fix the first sub connecting portion 124 and the second sub connecting portion 125. In some embodiments, the locking structure 126 is a snap, and the snap includes a bump and a groove disposed at the second end 1242 and the fourth end 1252, respectively, and the bump snaps into the groove to form a snap structure. In some embodiments, one of the second end 1242 and the fourth end 1252 is provided with a plurality of bumps, the plurality of bumps snap into the groove at different positions (i.e., the clasps snap together at different positions), and the first sub connecting portion 124 and the second sub connecting portion 125 form circular tube-shaped cavities of different diameters.

In some embodiments, the mother endoscope 3 may be fixed to the connecting device 1 by the locking structure 126. For example, the operator opens the locking structure of the first sub connecting portion 124 and the second sub connecting portion 125, places the mother endoscope 3 between the first sub connecting portion 124 and the second sub connecting portion 125 and snaps the first sub connecting portion 124 and the second sub connecting portion 125, so as to lock the locking structure to fix the mother endoscope 3.

In some embodiments, the inner diameter of the second connecting portion 12 is adjusted by the locking structure.

In some embodiments, when the mother endoscope 3 is fixed to the second connecting portion 12, the cavity formed by the snapping of the first sub connecting portion 124 and the second sub connecting portion 125 is narrowed by adjusting the locking structure 126, clamping the mother endoscope 3 within the cavity. Adjusting the locking structure 126 may include adjusting bolts, adjusting the snap position of the clasp, or the like. By adjusting the locking structure, the cavity formed by the snap-fit of the first sub connecting portion 124 and the second sub connecting portion 125 may be enlarged or reduced.

In some embodiments of the present disclosure, adjusting the size of the inner diameter of the second connecting portion by the locking structure may adapt the connecting device to mother endoscopes of different sizes. Thus, even if the size of the mother endoscope is changed or the placing direction is changed (e.g., tilted at a large angle), the problem of the mother endoscope slipping off may be avoided. In addition, the problem of the original connecting device not being fixed firmly due to the decrease in the elasticity of the second connecting portion or the decrease in the friction caused by the increase in the number of times the connecting device is used can be avoided.

In some embodiments of the present disclosure, fixing the mother endoscope by the first sub connecting portion, the second sub connecting portion, and the locking structure may further ensure that the mother endoscope is securely fastened, avoiding unexpected problems caused by the improper exertion of force when mounting and dismounting the mother endoscope.

Figure 8:
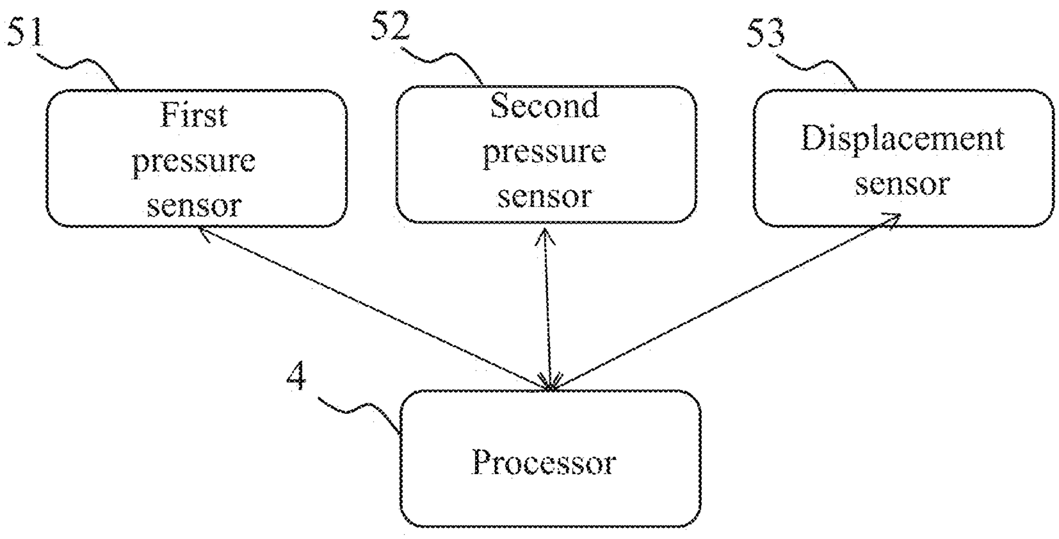
FIG. 8 is a schematic diagram of an exemplary endoscopic connecting system according to some embodiments of the present disclosure.

FIG. 8 is a schematic diagram of an exemplary endoscopic connecting system according to some embodiments of the present disclosure.

In some embodiments, the endoscopic connecting system includes a first pressure sensor 51, a second pressure sensor 52, and a processor 4.

The pressure sensor refers to a sensing device that may be used to detect pressure such as a piezoresistive pressure sensor, etc. In some embodiments, the first pressure sensor 51 is disposed on an inner wall of the first connecting portion 11. The first pressure sensor is configured to obtain a first pressure to which the first connecting portion is subjected. The first pressure may reflect the force acting on the baby endoscope when it is removed from the first connecting portion.

In some embodiments, the second pressure sensor 52 is disposed on an inner wall of the second connecting portion 12. The second pressure sensor 52 is configured to obtain a second pressure to which the second connecting portion is subjected. The second pressure may reflect the force acting on the mother endoscope when it is removed from the second connecting portion.

In some embodiments, the first pressure and the second pressure may be displayed on an interactive screen for reference by an operator, such as a doctor. The interactive screen is a display device in which the user controls the endoscope connecting system.

The processor 4 is configured to process data from at least one component of the endoscope connecting system or an external data source. For example, the processor may acquire and analyze the first pressure and the second pressure captured by the pressure sensor. As another example, the processor may acquire and process displacement data from the displacement sensor.

In some embodiments, the processor is communicatively connected with one or more of the first pressure sensor, the second pressure sensor, and the displacement sensor, respectively, to enable the transfer and exchange of information and/or data between each part. For example, the first pressure sensor may send the first pressure to the processor. As another example, the processor may send the first pressure to the interactive screen and display it on the interactive screen, etc. The communication linkage may include connecting via a network, for example, local area network CAN, Bluetooth, or the like.

In some embodiments, the processor may include a central processing unit (CPU), an application-specific integrated circuit (ASIC), an application-specific instruction set processor (ASIP), etc., or any combination thereof.

In some embodiments, the processor periodically acquires the first pressure and the second pressure or acquires the first pressure and the second pressure when the first pressure sensor and/or the second pressure sensor are triggered. The first pressure sensor and/or the second pressure sensor is triggered in response to the endoscope connecting system meeting a trigger condition.

The trigger condition refers to a condition in which the first pressure sensor or the second pressure sensor transmits the first pressure or the second pressure to the processor. In some embodiments, the trigger condition includes an instantaneous change in the first pressure and/or the second pressure that exceeds a change threshold. The instantaneous change in the first pressure or the second pressure may be determined by calculation. For example, the instantaneous change in the first pressure is the maximum of the difference in the first pressure per unit time. In some embodiments, the trigger condition includes the locking structure 126 in the second connecting portion 12 in an open state. In some embodiments, the processor may determine, via the second pressure, whether the locking structure 126 in the second connecting portion 12 is in the open state. For example, when the second pressure is within a locking pressure range, the locking structure 126 is in a locked state, otherwise it is in the open state. The change threshold and the locking pressure range may be determined by default by the processor or set by a technician.

In some embodiments, the processor is configured to issue an early warning in response to the first pressure and the second pressure meeting a predetermined condition.

The early warning refers to a notification message that suggests that there may be an abnormality in the connecting device. The early warning may include a text early warning or an audible early warning. In some embodiments, the operator may turn the early warning on or off via the interactive screen.

The predetermined condition refers to a condition that the first pressure or the second pressure satisfies when the early warning is required. In some embodiments, the predetermined condition includes a first predetermined condition and a second predetermined condition.

The first predetermined condition includes the first pressure being less than a first pressure threshold, or the second pressure being less than a second pressure threshold. In some embodiments, when one of the first pressure and the second pressure is less than each pressure threshold required for fixing, it may be considered that the mother endoscope or the baby endoscope and the connecting device are in an unconnected state. For example, the first pressure is greater than or equal to the first pressure threshold, but the second pressure is less than the second pressure threshold, which may indicate that the mother endoscope is fixed properly and the baby endoscope slips downwardly. As another example, the first pressure is less than the first pressure threshold, and the second pressure is greater than or equal to the second pressure threshold, which may indicate that the mother endoscope is loose or falling off, and the baby endoscope is fixed normally.

It is noted that in some embodiments, the first predetermined condition does not include a situation in which the first pressure is less than the first pressure threshold and the second pressure is less than the second pressure threshold, which may indicate that the connecting device is not in use. At this time, the processor may indicate on the interactive screen that the connecting device is not in use.

In some implementations, the second predetermined condition includes the first pressure being greater than or equal to a third pressure threshold, and/or the second pressure being greater than or equal to a fourth pressure threshold. The third pressure threshold is greater than the first pressure threshold, and the fourth pressure threshold is greater than the second pressure threshold. In some embodiments, when either or both of the first pressure and the second pressure are greater than the pressure required for fixing, it may be assumed that the mother endoscope and/or the baby endoscope are in a state of malfunctioning operation. For example, when the operator holding the endoscope is hit, causing both the first pressure and the second pressure to suddenly increase, exceeding the third pressure threshold and exceeding fourth pressure threshold, respectively, the first pressure and the second pressure satisfy the second predetermined condition, and the content of the early warning may be that the mother endoscope and the baby endoscope are collided by the external force and are unstable.

In some embodiments, the processor issues the early warning in response to the first pressure and the second pressure meeting any one of the predetermined conditions. In some embodiments, the content of the early warning matches the situation of the predetermined condition. For example, the content of the early warning is that the mother endoscope or the baby endoscope is loose when the first pressure and the second pressure satisfy the first predetermined condition. When the first pressure and the second pressure satisfy the second predetermined condition, the content of the early warning is a collision by the external force.

In some embodiments, the first pressure threshold, the second pressure threshold, the third pressure threshold, and the fourth pressure threshold are different for different operating scenarios.

The operating scenario refers to a scenario in which the baby endoscope and the mother endoscope are connected using the connecting device. The first pressure threshold, the second pressure threshold, the third pressure threshold, and the fourth pressure threshold may be determined based on the operation scenario. The operation scenario may include a scenario when performing a procedure using the endoscope, a scenario in which mounting or dismounting the endoscope, a scenario when adjusting the imaging catheter of the baby endoscope using the rotating wheel 25, etc. The first pressure threshold, the second pressure threshold, the third pressure threshold, and the fourth pressure threshold corresponding to the different operation scenarios may be determined by statistically analyzing historical pressure data for the different operation scenarios. For example, the processor may take the historical pressure data monitored in the operation scenarios, the maximum value of the pressure, as the first pressure threshold or the second pressure threshold; and add the maximum value of the pressure plus an error value as the third pressure threshold or the fourth pressure threshold. The error value may be determined by processor default or technician settings.

In some embodiments, the operating scenario may be manually set by a technician to determine the first pressure threshold, the second pressure threshold, the third pressure threshold, and the fourth pressure threshold that match the operating scenario.

In some embodiments, the processor may determine, through a pressure model, the first pressure threshold and the second pressure threshold.

The pressure model refers to a model for determining the first pressure threshold and the second pressure threshold. The pressure model may be a machine learning model, e.g., a long short-term memory (LSTM).

In some embodiments, an input of the pressure model includes a first pressure sequence and a second pressure sequence, and an output of the pressure model includes the first pressure threshold and the second pressure threshold. The first pressure sequence and the second pressure sequence may be sequences including the first pressures and the second pressures acquired by the first pressure sensor and the second pressure sensor, respectively, at a plurality of time points. More descriptions regarding the first pressure and the second pressure may be found hereinabove.

In some embodiments, the pressure model may be obtained by training with training samples and labels. In some embodiments, the process of training the pressure model may be done on a remote server or an outside server. The trained pressure model may be stored in a processor of the connecting device, thereby conserving processor power. The training samples may include a sample first pressure sequence and a sample second pressure sequence, and the labels may be a first pressure threshold and a second pressure threshold corresponding to the training samples. In some embodiments, the processor may determine the training samples of historical different operating scenarios based on a historical first pressure sequence and a historical second pressure sequence of the historical different operating scenarios. In some embodiments, the processor may obtain labels by experiments. For example, when mounting or dismounting the endoscope, the operation scenario in which the endoscope slips or loosens may be created by a manipulator, or the like. The processor may capture the first pressure of the first connecting portion and the second pressure of the second connecting portion and take the average of a larger value and a plurality of smaller values of the first pressure and the second pressure, respectively, and use them as labels (e.g., as corresponding first pressure threshold and second pressure threshold). The first pressure and the second pressure that are greater than a predetermined acquisition pressure threshold are considered to be greater values, and the first pressure and the second pressure that are less than the predetermined acquisition pressure threshold are considered to be smaller values.

In some embodiments, the first pressure threshold and the second pressure threshold are also related to the operation scenario. The training samples of different operation scenarios correspond to different first pressure thresholds and second pressure thresholds. The labels corresponding to the training samples of the different operation scenarios may also include types of the different operation scenarios.

In some embodiments, the processor may obtain a training dataset, the training dataset including a plurality of training samples and labels corresponding to each of the plurality of training samples. The processor may perform a plurality of rounds of iterations. At least one round of iteration includes selecting, from the training dataset, one or more training samples, inputting the one or more training samples into the pressure model, and obtaining a predicted output of the pressure model corresponding to the one or more training samples; calculating a value of a predefined loss function by substituting the predicted output of the pressure model corresponding to the one or more training samples, as well as the labels of the one or more training samples, into a formula of the loss function; inversely updating, based on the value of the loss function, model parameters of the pressure model. The iteration may be performed using various manners, for example, updating based on a gradient descent algorithm. When an end condition of the iteration is satisfied, the iteration is ended, and the trained and completed pressure model is obtained.

In some embodiments, the processor may determine the third pressure threshold and the fourth pressure threshold based on the first pressure threshold and the second pressure threshold obtained through the pressure model. For example, the third pressure threshold is the first pressure threshold plus the error value, and the fourth pressure threshold is the second pressure threshold plus the error value.

In some embodiments of the present disclosure, by the pressure model, a more accurate first pressure threshold and second pressure threshold may be obtained, which makes the judgment of the early warning more accurate.

In some embodiments of the present disclosure, determining whether to issue the early warning by a predetermined condition is helpful in preventing problems such as damage to endoscopes, misalignment of devices, or the like.

In some embodiments, the endoscope connecting system includes a displacement sensor 53.

The displacement sensor 53 refers to a sensor that is capable of measuring the position or movement data of the endoscopic main scope. For example, the displacement sensor 53 may include a strain displacement sensor, a grating sensor, a Hall displacement sensor, or the like. In some embodiments, the displacement sensor 53 is disposed at the front end of the mother endoscope 3, and the displacement sensor 53 is capable of acquiring displacement data of the mother endoscope 3 when the mother endoscope 3 moves.

In some embodiments, the processor is configured to control turning on the displacement sensor at a time point when the mother endoscope begins to be utilized; acquire continuous displacement data transmitted by the displacement sensor while the mother endoscope is moving; processing the displacement data to generate a three-dimensional path, the three-dimensional path characterizing a movement path of the mother endoscope.

In some embodiments, the processor may determine the time point when the mother endoscope begins to be utilized in a variety of ways. The time point when the mother endoscope begins to be used is the time point when the mother endoscope is powered on and activated. For example, the processor may confirm that the mother endoscope begins to be used when the second pressure obtained by the second pressure sensor is greater than the second pressure threshold. As another example, the processor may directly read, via the endoscope connecting system, the operating state of the mother endoscope, thereby determining the time point when the mother endoscope begins to be used. Controlling the turn-on of the displacement sensor at the time point when the mother endoscope is in use prevents the displacement sensor from acquiring unexpected displacement data.

In some embodiments, the displacement sensor continuously transmits successive displacement data outwardly, the displacement data including a displacement signal. The time interval required for two adjacent outward transmissions of the displacement sensor is a transmission period. For example, the transmission period is 3 seconds, 5 seconds, etc. The transmission period may be pre-stored, and the processor may use it directly.

In some embodiments, the processor determines, based on the early warning, a transmission period in which the displacement sensor transmits successive displacement data outwardly. Merely by way of example, the processor may determine the transmission period based on the cumulative count of occurrences of the early warning per unit of time through a predetermined relationship. The predetermined relationship includes a correspondence between the cumulative count of occurrences of the early warning per unit of time and the transmission period. For example, the predetermined relationship is that the higher the cumulative count of occurrences of the early warning per unit of time, the shorter the transmission period.

In some embodiments, the processor adjusts the transmission period of the displacement data based on the early warning by a predetermined algorithm. Merely by way of example, the predetermined algorithm includes shortening the transmission period in response to receiving the early warning. Receiving the early warning indicates a change in the position of the endoscope, at which point shortening the transmission cycle allows accurate acquisition of the displacement data.

In some embodiments, the predetermined algorithm includes the following equation.

$$T2 = T1/(1 + i).$$

Where T2 denotes a shortened transmission period, T1 denotes a transmission period before being shortened, and i denotes a warning factor.

In some embodiments, the warning factor i is determined based on the early warning. In some embodiments, the warning factor i is determined based on the cumulative count of occurrences of the early warning, and a value of the type of the early warning. The value of the type of the early warning may include slipping, loosening, and sudden condition. Merely by way of example, the warning factor is a weighted sum of value of the type and the cumulative count of occurrences of the early warning. The weighting of the type value for each early warning may be pre-set by the technician.

In some embodiments, the processor may determine or adjust the transmission period for the displacement sensor to transmit successive displacement data outwardly based on operational data. The operational data refers to data related to the operation of the endoscope. For example, the operation data includes statistics on the cumulative operation time, the total length of entry into the body, or the like. Merely by way of example, the magnitude of the transmission period is negatively correlated to the operational data, i.e., the longer the cumulative operation time of the operational data, and the longer the total length of the entry into the human body, the smaller the transmission period.

In some embodiments, the processor may process the displacement data to generate a three-dimensional path, the three-dimensional path characterizing the travel path of the mother endoscope. The processor may generate the three-dimensional path in a variety of ways. Merely by way of example, the processor may perform a coordinate system transformation on the displacement data; perform data fusion or computation on the displacement data after the coordinate system transformation to obtain the three-dimensional path; visualize the three-dimensional path to obtain a visualized three-dimensional path. In some embodiments, before the processor generates the three-dimensional path, the displacement data with a displacement of 0 or a displacement anomaly may be removed to alleviate the amount of data processing. The data with a displacement of 0 in the displacement data may be the displacement data acquired between the power-on of the mother endoscope and the start of movement of the mother endoscope.

In some embodiments, the processor may also scan patient information in advance, so as to obtain a three-dimensional model of the patient by the three-dimensional modeling on the patient, and fuse the three-dimensional path with the three-dimensional model of the patient, to obtain a phase position of the three-dimensional path of the endoscope and the three-dimensional model of the patient, thus determining the three-dimensional position of the endoscope in the patient. The processor may determine the three-dimensional model of the patient, e.g., by an image acquisition device (e.g., a three-dimensional camera). The processor fusing the three-dimensional path with the three-dimensional model of the patient further includes that the processor removes the path before the endoscope enters into the patient's body and retains only the three-dimensional path after the endoscope enters into the patient's body. Merely by way of example, the processor may retain only the displacement data after a displacement value exceeds a displacement threshold. The displacement threshold may be a distance between a front end of the endoscope and a natural lumen entrance of the human body at the time of the activation of the endoscope.

In some embodiments of the present disclosure, by setting the displacement sensor, the doctor may be informed in real time of the path that the endoscope has already traveled inside the patient's body, as well as the current three-dimensional position of the endoscope in the patient's body. In addition, the doctor may be assisted in carrying out the relevant surgical operation.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements, and amendments to the present disclosure. These alterations, improvements, and amendments are intended to be suggested by this disclosure and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure, or feature described in connection with the embodiment is included in at least one embodiment of the present disclosure. Therefore, it is emphasized and should be appreciated that two or more references to "an embodiment", "one embodiment", or "an alternative embodiment" in various portions of the present disclosure are not necessarily all referring to the same embodiment. In addition, some features, structures, or characteristics of one or more embodiments in the present disclosure may be properly combined.

Furthermore, the recited order of processing elements or sequences, or the use of numbers, letters, or other designations, therefore, is not intended to limit the claimed processes and methods to any order except as may be specified in the claims. Although the above disclosure discusses some embodiments of the invention currently considered useful by various examples, it should be understood that such details are for illustrative purposes only, and the additional claims are not limited to the disclosed embodiments. Instead, the claims are intended to cover all combinations of corrections and equivalents consistent with the substance and scope of the embodiments of the present disclosure. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that object of the present disclosure requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about", "approximate", or "substantially". For example, "about", "approximate", or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes. History application documents that are inconsistent or conflictive with the contents of the present disclosure are excluded, as well as documents (currently or subsequently appended to the present specification) limiting the broadest scope of the claims of the present disclosure. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A connecting device, comprising:

a first connecting portion configured to connect a baby endoscope;

a second connecting portion connected to the first connecting portion, wherein the second connecting portion encloses to form a socket cavity, the second connecting portion is connected to a first opening and a second opening of the socket cavity, an area of a cross-section of the socket cavity increases in a direction from the first opening to the second opening, the second connecting portion is configured to be socketed to a mother endoscope through the socket cavity, the second connecting portion is connected with the mother endoscope, and the second connecting portion is provided in any one of the following ways:

the second connecting portion is a closed ring, and an outer wall of the second connecting portion is connected to the first connecting portion; and the second connecting portion is provided with a first notch, the first notch is connected to the socket cavity, the first notch extends from the first opening to the second opening, and a side of the second connecting portion opposite the first notch is connected to the first connecting portion;

a sheath, wherein the sheath is a flexible body, the sheath is at least partially disposed within the socket cavity, and in a state in which the second connecting portion is connected with the mother endoscope, the sheath is compressed between the mother endoscope and an inner wall of the socket cavity;

wherein the sheath has a sheath body and two port wrapping ribs, the sheath body includes two ports, each of the two ports is provided with each of the two port wrapping ribs, and in a state in which the sheath is connected with the second connecting portion, the sheath body is affixed to the inner wall of the socket cavity, and the two port wrapping ribs cover an end face of an edge of the first opening of the second connecting portion and an end face of an edge of the second opening of the second connecting portion.

2. The connecting device of claim 1, wherein the first notch is an elongate opening; and a width of the first notch is not less than an outer diameter of a localized structure of the mother endoscope, such that the mother endoscope is capable of extending into the socket cavity through the elongate opening.

3. The connecting device of claim 1, wherein a second notch is provided on the sheath body, the second notch is connected to each of the two ports;

the sheath includes a notch wrapping rib disposed on the sheath body, and the notch wrapping rib is disposed on an edge of the second notch; and in the state in which the sheath is connected with the second connecting portion, the notch wrapping rib covers an end face in a thickness direction of the first notch of the second connecting portion.

4. The connecting device of claim 1, wherein the first connecting portion includes a main housing and a plurality of tabs;

the second connecting portion is connected to the main housing;

each of the plurality of tabs is connected to the main housing, and each of the plurality of tabs is spaced in turn along a circumference of an edge of the main housing; and in a state in which the first connecting portion is connected with the baby endoscope, the main housing is affixed to the baby endoscope, and each of the plurality of tabs is snap-fit to an outer wall surface of a medical device.

5. The connecting device of claim 4, wherein a reinforcing rib is provided on a side of the main housing back away from the second connecting portion.

6. The connecting device of claim 4, wherein a reinforcing back plate is provided on a side of the main housing back away from each of the plurality of tabs; and the second connecting portion is connected to the reinforcing back plate.

7. The connecting device of claim 4, wherein the baby endoscope includes a plurality of functional portions; and in the state in which the first connecting portion is connected with the baby endoscope, at least a portion of the plurality of functional portions is disposed on an opening formed between adjacent tabs.

8. The connecting device of claim 4, wherein the baby endoscope is provided with a pincer channel nozzle that protrudes outward having a pincer channel opening; and in the state in which the first connecting portion is connected with the baby endoscope, one of the plurality of tabs is snapped to an outer wall surface of the pincer channel nozzle.

9. The connecting device of claim 1, wherein two sides of the first connecting portion are provided with a first side edge and a second side edge along a width direction; and a distance between the second connecting portion and the first side is less than a distance between the second connecting portion and the second side edge.

10. An endoscope connecting system, comprising:

the connecting device of claim 1; and the baby endoscope detachably connected with the first connecting portion of the connecting device.

11. The endoscope connecting system of claim 10, further comprising:

a mother endoscope being detachably connected with the second connecting portion.

12. The endoscope connecting system of claim 11, wherein a disassembling direction of the baby endoscope and the first connecting portion is different from a disassembling direction of the mother endoscope and the second connecting portion.

13. The endoscopic connecting system of claim 12, wherein the baby endoscope is dissembled from the first connecting portion by applying a force in a horizontal direction along an operating handle of the baby endoscope.

14. The endoscope connecting system of claim 13, wherein the mother endoscope is dissembled from the second connecting portion by applying a force in a vertical direction along an imaging catheter of the mother endoscope.

* * * * *